US009096640B2

(12) United States Patent
Klar et al.

(10) Patent No.: US 9,096,640 B2
(45) Date of Patent: Aug. 4, 2015

(54) 17-HYDROXY-17-PENTAFLUOROETHYL-ESTRA-4,9(10)-DIENE-11-METHYLENE OXYALKYLENE ARYL DERIVATIVES, PROCESS FOR PREPARATION THEREOF, AND USE THEREOF FOR TREATMENT OF DISEASES

(75) Inventors: Ulrich Klar, Berlin (DE); Wolfgang Schwede, Glienicke (DE); Carsten Möller, Berlin (DE); Andrea Rotgeri, Berlin (DE); Wilhelm Bone, Berlin (DE)

(73) Assignee: Bayer Intellectual Property, Monheim (DE)

(*) Notice: Subject to any disclaimer, the term of this patent is extended or adjusted under 35 U.S.C. 154(b) by 465 days.

(21) Appl. No.: 13/384,765

(22) PCT Filed: Jul. 7, 2010

(86) PCT No.: PCT/EP2010/004146
§ 371 (c)(1),
(2), (4) Date: Apr. 5, 2012

(87) PCT Pub. No.: WO2011/009529
PCT Pub. Date: Jan. 27, 2011

(65) Prior Publication Data
US 2012/0184515 A1    Jul. 19, 2012

(30) Foreign Application Priority Data

Jul. 20, 2009 (DE) .......................... 10 2009 034 366

(51) Int. Cl.
| A61K 31/567 | (2006.01) |
| C07J 1/00 | (2006.01) |
| C07J 7/00 | (2006.01) |
| C07J 41/00 | (2006.01) |
| C07J 43/00 | (2006.01) |
| A61K 31/573 | (2006.01) |

(52) U.S. Cl.
CPC .............. *C07J 1/0081* (2013.01); *C07J 7/0085* (2013.01); *C07J 41/0083* (2013.01); *C07J 41/0094* (2013.01); *C07J 43/003* (2013.01); *A61K 31/573* (2013.01)

(58) Field of Classification Search
CPC ..... C07J 7/0085; C07J 41/005; A61K 31/573
USPC .................. 552/520, 598, 642; 514/179, 182
See application file for complete search history.

(56) References Cited

U.S. PATENT DOCUMENTS

| 4,386,085 | A | 5/1983 | Teutsch et al. |
| 4,609,651 | A | 9/1986 | Rohde et al. |
| 4,634,695 | A | 1/1987 | Torelli et al. |
| 4,900,725 | A | 2/1990 | Nioue et al. |
| 4,921,846 | A | 5/1990 | Nedelec et al. |
| 4,954,490 | A | 9/1990 | Cook et al. |
| 5,073,548 | A | 12/1991 | Cook et al. |
| 5,108,996 | A | 4/1992 | Claussner et al. |
| 5,272,140 | A | 12/1993 | Loozen |
| 5,407,928 | A | 4/1995 | Kasch et al. |
| 5,576,310 | A | 11/1996 | Schubert et al. |
| 5,693,628 | A | 12/1997 | Schubert et al. |
| 5,712,264 | A | 1/1998 | Hamersma et al. |
| 5,739,125 | A | 4/1998 | Kasch et al. |
| 5,986,115 | A | 11/1999 | Bohlmann et al. |
| 6,020,328 | A | 2/2000 | Cook et al. |
| 6,042,324 | A | 3/2000 | Aggarwal et al. |
| 6,225,298 | B1 | 5/2001 | Spicer et al. |
| 6,316,432 | B1 | 11/2001 | Schwede et al. |
| 6,476,079 | B1 | 11/2002 | Jukarainen et al. |
| 6,503,895 | B2 | 1/2003 | Schwede et al. |
| 6,806,263 | B2 | 10/2004 | Schwede et al. |
| 6,825,182 | B2 | 11/2004 | Ring et al. |
| 6,861,415 | B2 | 3/2005 | Kim et al. |
| 7,087,591 | B2 | 8/2006 | Kim et al. |
| 7,148,213 | B2 | 12/2006 | Schwede et al. |
| 7,192,942 | B2 | 3/2007 | Grawe et al. |
| 7,550,451 | B2 | 6/2009 | Hillisch et al. |

(Continued)

FOREIGN PATENT DOCUMENTS

| CA | 2280041 C | 8/1998 |
| DE | 19706061 A1 | 8/1998 |

(Continued)

OTHER PUBLICATIONS

Ulrike Fuhrmann, Holger Hess-Stumpp, Arwed Cleve, Günter Neef, Wolfgang Schwede, Jens Hoffmann, Karl-Heinrich Fritzemeir, Kristof Chwalisz, "Sythesis and Biological Activity of a Novel, highly Potent Progesterone Receptor Antiagonist," J. Med. Chem., vol. 43, pp. 5010-5016 (2000).

Jody Steinauer, Elizabeth A. Pritts, Rebecca Jackson, Alison F. Jacoby, "Systematic review of mifepristone for the treatment of uterine leiomyomata," Obstet Gynecol, vol. 103, No. 6, pp. 1331-1336 (Jun. 2004).

Kristof Chwalisz, Lois Larsen, Cynthia Mattia-Goldberg, Anthony Edmonds, Walter Elger, and Craig A. Winkel, "A randomized, controlled trial of asoprisnil, a novel selective progesterone receptor modulator, in women with uterine leiomyomata," Fertil Steril, vol. 87, No. 6, pp. 1399-1412 (Jun. 2007).

L. Michael Kettel, Ana A. Murphy, Joseph F. Mortola, James H. Liu, AndréUlmann, and Samuel S.C. Yen, "Endocrine responses to long-term administration of the antiprogesterone RU486 in patients with pelvic endometriosis," Fertil Steril, vol. 56, No. 3, pp. 402-407 (Sep. 1991).

(Continued)

*Primary Examiner* — Barbara P Badio
(74) *Attorney, Agent, or Firm* — Karen B. King; Thomas C. Blankinship

(57) ABSTRACT

The invention relates to 17-hydroxy-17-pentafluoroethyl-estra-4,9(10)-diene-11-methyleneoxyalkylenearyl derivative of the formula I with progesterone-antagonising action and to processes for preparation thereof, to use thereof for treatment and/or prophylaxis of disorders and to the use thereof for production of medicaments for treatment and/or prophylaxis of disorders, especially of fibroids of the uterus (myomas, uterine leiomyomas), endometriosis, heavy menstrual bleeds, meningiomas, hormone-dependent breast cancers and complaints associated with the menopause, or for fertility control and emergency contraception.

12 Claims, No Drawings

(56) References Cited

U.S. PATENT DOCUMENTS

| | | | |
|---|---|---|---|
| 7,799,770 | B2 | 9/2010 | Grawe et al. |
| 7,910,573 | B2 | 3/2011 | Beckmann et al. |
| 8,053,426 | B2 | 11/2011 | Fuhrmann et al. |
| 2001/0001657 | A1 | 5/2001 | Schneider et al. |
| 2001/0016578 | A1 | 8/2001 | Spicer et al. |
| 2002/0045774 | A1 | 4/2002 | Schwede et al. |
| 2002/0143000 | A1 | 10/2002 | Hegele-Hartung |
| 2003/0069434 | A1 | 4/2003 | Bohlmann et al. |
| 2003/0191099 | A1 | 10/2003 | Bohlmann et al. |
| 2004/0006241 | A1 | 1/2004 | Grawe |
| 2004/0048841 | A1 | 3/2004 | Hoffmann |
| 2004/0157811 | A1 | 8/2004 | Lichtner |
| 2005/0080060 | A1 | 4/2005 | Schwede |
| 2005/0277769 | A1 | 12/2005 | Burton et al. |
| 2007/0105828 | A1 | 5/2007 | Joshi et al. |
| 2009/0075989 | A1 | 3/2009 | Schwede et al. |
| 2011/0112057 | A1 | 5/2011 | Fuhrmann et al. |
| 2012/0149670 | A1 | 6/2012 | Schwede et al. |
| 2012/0190660 | A1 | 7/2012 | Klar et al. |
| 2012/0232042 | A1 | 9/2012 | Klar et al. |
| 2012/0258941 | A1 | 10/2012 | Klar et al. |
| 2012/0316145 | A1 | 12/2012 | Klar et al. |
| 2013/0005697 | A1 | 1/2013 | Schwede et al. |
| 2013/0072464 | A1 | 3/2013 | Schwede et al. |

FOREIGN PATENT DOCUMENTS

| | | |
|---|---|---|
| DE | 10221034 A1 | 11/2003 |
| EP | 0411733 B1 | 2/1991 |
| EP | 0676203 A1 | 10/1995 |
| EP | 909764 A1 | 4/1999 |
| EP | 0970103 B1 | 1/2000 |
| EP | 1862468 | 12/2007 |
| IN | 978/MUM/2005 | 8/2005 |
| JP | H11171774 A | 6/1999 |
| WO | 9603130 A1 | 2/1996 |
| WO | 9615794 | 5/1996 |
| WO | 9623503 A1 | 8/1996 |
| WO | 98/05679 A2 | 2/1998 |
| WO | 9807740 | 2/1998 |
| WO | 98/26783 A1 | 6/1998 |
| WO | 98/34947 A1 | 8/1998 |
| WO | 9933855 | 7/1999 |
| WO | 99/53924 A1 | 10/1999 |
| WO | 01/47490 A1 | 7/2001 |
| WO | 02/32429 A2 | 4/2002 |
| WO | 03045972 A1 | 6/2003 |
| WO | 03093292 | 11/2003 |
| WO | 2004014935 A1 | 2/2004 |
| WO | 2006/010097 A2 | 1/2006 |
| WO | 2008/058767 A1 | 5/2008 |
| WO | 2009138186 A2 | 11/2009 |
| ZA | 977482 | 2/1998 |

OTHER PUBLICATIONS

L. Michael Kettel, Ana A. Murphy, Arlene J. Morales, AndréUlmann, Etienne E. Baulieu, and Samuel S.C. Yen, "Treatment of endometriosis with the antiprogesterone mifepristone (RU486)," Fertil Steril, vol. 65, No. 1, pp. 23-28 (Jan. 1996).

L. Michael Kettel, Ana A. Murphy, Arlene J. Morales, and Samuel S.C. Yen, "Preliminary report on the treatment of emdomietriosis with low-dose mifeprostone (RU 486),". Am J Gynecol, vol. 178, No. 6, pp. 1151-1156 (Jun. 1998).

Carsten Möller, Jens Hoffmann, Thomas A Kirkland and Wolfgang Schwede, "Investigational developments for the treatment of progesterone-dependent diseases,"Expert Opin. Investig. Drugs., vol. 17, No. 4, pp. 469-479 (2008).

Madhu Bagaria, Amita Suneja, Neelam B. Vaid, Kiran Guleria, and Kiran Mishra, Low-dose mifepristone in treatment of uterine leiomyoma: A randomised double-blind placebo-controlled clinical trial, The Royal Australian and New Zealand College of Obstetricians and Gynaecologists, vol. 49, pp. 77-83 (2009).

Ana A. Murphy, L. Michael Kettel, Arlene J. Morales, Veronica J. Roberts and Samuel S.C. Yen, "Regression of Uterine Leiomyomata in Response to the Antiprogesterone RU 486," J. Clin. Endocrinol. Metab., vol. 76, No. 2, pp. 513-517 (1993).

M. Bohl, G. Schubert, K. Ponsold, G. Reck, E. Höhne, and K. Simon, "Molecular mechanics and X-ray crystal structure investigations on conformations of 11β substituted 4,9-dien-3-one steroids," J. Mol. Graphics, vol. 7, pp. 122-153 (Sep. 1989).

Dario Braga and Joel Bernstein, "3.3 Crystal Polymorphism: Challenges at the Crossroads of Science and Technology," Making Crystals by Design (Dario Braga and Fabrizia Grepioni eds., Wiley-VCH Verlag GmbH & Co. KgaA, Weinheim, Germany), pp. 293-314 (2007).

Walter Cabri, Paolo Ghetti, Giovanni Pozzi, and Marco Alpegiani, "Polymorphisms and Patent, Market, and Legal Battles: Cefdinir Case Study," Organic Process Research & Devel., vol. 11, No. 1, pp. 64-72 (2007).

Mino R. Caira, "Crystalline Polymorphism of Organic Compounds," Topics in Current Chemistry, vol. 198, pp. 164-208 (1998).

R.J. Davey, "Solvent Effects in Crystallization Processes," Current Topics in Material Science, vol. 8, pp. 429-479 (1982).

English Translation of Office Action for European Application No. 06090095.8 dated Jan. 16, 2007.

Braja G. Hazra and Vandana S. Pore, "Mifepristone (RU-486), the recently developed antiprogesterone drug and tis analogues," J. Indian Inst. Sci., vol. 81, pp. 287-298 (May-Jun. 2001).

English Language Abstract of Japanese Patent Publication JP11171774 (corresponding to Japanese Patent Application No. 19970335723 filed Dec. 5, 1997) by Kyowa Hakko Kogyo Co. Ltd., published Jun. 29, 1999.

R. Maibauer, C. Zurth, M. Schultze-Mosgau, B. Rohde, I. Kuss, and W. Sittner, "First human data for ZK 230211 (ZK-PRA), a new progesterone receptor antagonist: a phase I clinical analysis of safety and pharmacokinetics in healthy postmenopausal women," Abstracts—Poster Session IV, 29th Annual San Antonio Breast Cancer Symposium, Dec. 14-17, 2006.

David K. Tellekson, Elizabeth A. Richardson, and Sandra S. Lee, "Strategies for Attacking and Defending Pharmaceutical Patents: A Modern Take on 'The Art of War,'" Int. Property & Techn. Law Journal, vol. 17, No. 12, pp. 5-14 (Dec. 2005).

English Language Translation of EP0411733, 1991.
English Language Translation of EP0676203, 1995.
English Language Translation of WO1998/026783.
English Language Translation of WO1999/053924.

V.J. Van Geerstein, J.A. Kanters, P. Van Der Sluis, and J. Kroon, "Structure of the n-Butyl Acetate Solvate of 11β-[4-(Dimethylamino)phenyl]-17β-hydroxy-17α-(1-propynyl)estra-4,9-dien-3-one," Acta Cryst., C42, pp. 1521-1523 (1986).

Sudha R. Vippagunta, Harry G. Brittain, David J.W. Grant, "Crystalline Solids," Adv. Drug Delivery Reviews, vol. 48, pp. 3-26 (2001).

George A. Patani and Edmond J. Lavoie, "Bioisosterism: A Rational Approach in Drug Design," Chem. Rev., vol. 96, pp. 3147-3176 (1996).

Braja, et al., "Mifepristone [RU-486), the recently developed antiprogesterone drug and its analogues," J. Indian Inst. Sci., 2001, 81:287-289.

U.S. Appl. No. 13/384,332, 371(c) date Jun. 4, 2012, published as US 2012-0232042.

U.S. Appl. No. 13/386,420 371(c) date Apr. 5, 2012, published as US 2012-0190660.

U.S. Appl. No. 13/386,031 371(c) Aug. 28, 2012, published as US 2012-0316145.

U.S. Appl. No. 13/386,421 371(c) date Jun. 25, 2012, published as US 2012-0258941.

U.S. Appl. No. 13/376,512, 371(c) date Feb. 27, 2012, published as US 2012-0149670.

U.S. Appl. No. 13/577,799, 371(c) date Sep. 21, 2012, published as US 2013-0005697.

U.S. Appl. No. 13/578,500 371(c) date Oct. 1, 2012, published as US 2013-0072464.

17-HYDROXY-17-PENTAFLUOROETHYL-ESTRA-4,9(10)-DIENE-11-METHYLENE OXYALKYLENE ARYL DERIVATIVES, PROCESS FOR PREPARATION THEREOF, AND USE THEREOF FOR TREATMENT OF DISEASES

The invention relates to 17-hydroxy-17-pentafluoroethyl-estra-4,9(10)-diene-11-methyleneoxyalkylenearyl derivative of the formula I with progesterone-antagonising action and to processes for preparation thereof, to use thereof for treatment and/or prophylaxis of disorders and to the use thereof for production of medicaments for treatment and/or prophylaxis of disorders, especially of fibroids of the uterus (myomas, uterine leiomyomas), endometriosis, heavy menstrual bleeds, meningiomas, hormone-dependent breast cancers and complaints associated with the menopause, or for fertility control and emergency contraception.

These compounds are valuable active pharmaceutical ingredients. They can be used, inter alia, for production of pharmaceutical formulations for treatment of fibroids of the uterus or of endometriosis, heavy menstrual bleeds, meningiomas, hormone-dependent breast cancers and complaints associated with the menopause, or for fertility control and emergency contraception. For treatment of uterus fibroids and of endometriosis, the inventive compounds can also be administered sequentially in combination with gestagens. Within such a treatment regime, the inventive compounds could be administered over a period of 1-6 months, followed by a pause in treatment or sequential treatment with a gestagen over a period of 2-6 weeks, or followed by treatment with an oral contraceptive (OC combinations) over the same period.

The efficacy of the inventive compounds as a progesterone receptor antagonist has been shown in vitro in transactivation tests.

Compounds with antagonistic action on the progesterone receptor (competitive progesterone receptor antagonists) became known for the first time in 1982 (RU 486; EP57115) and have been described many times since then. Progesterone receptor antagonists with a fluorinated 17a side chain were published in WO 98/34947 and Fuhrmann et al., J. Med. Chem. 43, 5010-5016 (2000).

The compounds with a fluorinated 17α side chain described in WO 98/34947 generally have very strong antagonistic activity on the progesterone receptor. Compounds which are very potent and are therefore preferred in WO 98/34947 are 11β-(4-acetylphenyl)-20,20,21,21,21-pentafluoro-17-hydroxy-19-nor-17α-pregna-4,9-dien-3-one, 11β-(4-acetylphenyl)-20,20,21,21,21-pentafluoro-17-hydroxy-19-nor-17α-pregna-4-en-3-one and 6'-acetyl-9,11β-dihydro-17β-hydroxy-17α-(1,1,2,2,2-pentafluoroethyl)-4'H-naphth[3',2',1':10,9,11]ester-4-en-3-one. These compounds are converted to various metabolites to a considerable degree in vivo, some of which have strong pharmacological activity, some of them lesser pharmacological activity. The metabolism occurs predominantly at the 4 substituent of the 11-phenyl radical. WO2008/058767 describes compounds of which at least some are metabolites of the compounds described in WO 98/34947.

It is an object of the present invention to provide highly potent competitive progesterone receptor antagonists and hence alternative possible treatments of gynaecological disorders.

It has been found that the inventive compounds are particularly suitable for achieving this object.

The present invention relates to 17-hydroxy-17-pentafluoroethyl-estra-4,9(10)-diene-11-methyleneoxyalkylenearyl derivatives with the general chemical formula I:

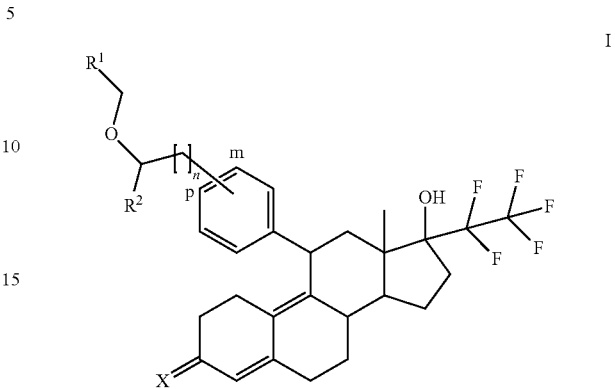

in which
the phenyl substituent bearing the $R^1$ and $R^2$ radicals is joined to the phenyl ring in the m or p position,
n is 0 or 1,
$R^1$ is hydrogen, $C_1$-$C_{10}$-alkyl, $CH_2OR^4$, $CO_2R^5$, CN, aryl or heteroaryl,
$R^2$ is hydrogen or $C_1$-$C_{10}$-alkyl,
X is oxygen, an $NOR^3$ or $=NNHSO_2R^3$ group,
$R^3$ is hydrogen, $C_1$-$C_{10}$-alkyl, aryl or $C_7$-$C_{20}$-aralkyl,
$R^4$ is hydrogen, —$CH_2$—$CH_2$—OH or $CH_2CO_2R^5$,
$R^5$ is hydrogen or $C_1$-$C_{10}$-alkyl,
and the stereoisomers, solvates, salts or solvates of the salts thereof, including all crystal polymorphs, the α-, β- or γ-cyclodextrin clathrates, and the compounds encapsulated with liposomes.

In a preferred embodiment of the invention, X is selected from the group comprising oxygen, $NOR^3$ and $NNHSO_2R^3$. In a further preferred embodiment of the invention, X is oxygen.

Depending on their structure, the inventive compounds of the general formula I can exist in stereoisomeric forms (enantiomers, diastereomers). The invention therefore encompasses the enantiomers or diastereomers and the particular mixtures thereof, including the racemates. It is possible to isolate the stereoisomerically homogeneous constituents from such mixtures of enantiomers and/or diastereomers in a known manner.

Each of the substituents on the steroid backbone mentioned may be either in an a position or in a β position. In addition, it is also possible for the substituents on the steroid backbone which contain a double bond and in which the double bond bears at least one non-hydrogen substituent on each atom to be present either in E or Z configuration.

When the inventive compounds can occur in tautomeric forms, the present invention encompasses all tautomeric forms.

Preferred salts in the context of the present invention are physiologically compatible salts of the inventive compounds. Also included, however, are salts which are themselves unsuitable for pharmaceutical applications but can be used, for example, for the isolation or purification of the inventive compounds.

Physiologically compatible salts of the inventive compounds include—when a basic function is present—salts with inorganic or organic acids, especially of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid or benzoic acid.

Physiologically compatible salts of the inventive compounds include—when an acidic acid function is present—alkali metal salts, alkaline earth metal salts or ammonium salts, as obtainable by reaction with corresponding inorganic or organic bases. Preferred examples include alkali metal salts (e.g. sodium and potassium salts), alkaline earth metal salts (e.g. calcium and magnesium salts) and ammonium salts derived from ammonia or organic amines having 1 to 16 carbon atoms, preferred examples being ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, D-methylglucamine, ethylglucamine, 1,6-hexadiamine, glucosamine, N-methylglycine, 2-amino-1,3-propanediol, tris(hydroxymethyl) aminomethane and 1-amino-2,3,4-butanetriol.

Solvates in the context of the invention refer to those forms of the inventive compounds which, in the solid or liquid state, exhibit adduct formation with solvent molecules. The solvent may be in a stoichiometric or else nonstoichiometric ratio. In the case of stoichiometric solvates, reference is also made to hemi- (semi-), mono-, sesqui-, di-, tri-, tetra-, pentasolvates, etc. Hydrates are a specific form of the solvates in which the coordination is with water.

The present invention also encompasses prodrugs of the inventive compounds. The term "prodrugs" encompasses compounds which, during their time of residence in the body, are converted to inventive compounds, for example by enzymatic or hydrolytic processes.

In the context of the present invention, the substituents, unless specified otherwise, are each defined as follows:

Alkyl represents straight- or branched-chain alkyl groups having 1-6 carbon atoms, for example methyl, ethyl, propyl, isopropyl, n-butyl, sec-butyl, isobutyl, tert-butyl, n-pentyl, isopentyl, neopentyl, hexyl, heptyl, octyl, nonyl and decyl.

Aryl is a mono- to tricyclic aromatic substituted or unsubstituted carbocyclic radical, for example phenyl, naphthyl, which may be mono- or polysubstituted by halogen (F, Cl, Br, I), OH, O-alkyl, $CO_2H$, $CO_2$-alkyl, $NH_2$, $NH(C_1$-$C_{10}$-alkyl), $N(C_1$-$C_{10}$-alkyl)$_2$, especially $N(CH_3)_2$, $NO_2$, $N_3$, ON, $C_1$-$C_{10}$-alkyl, $C_1$-$C_{10}$-perfluoroalkyl, $C_1$-$C_{10}$-acyl, $C_1$-$C_{10}$-acyloxy groups.

Heteroaryl is an aromatic mono- or bicyclic radical having generally 5 to 10 and preferably 5 to 6 ring atoms and up to 5, preferably up to 4, heteroatoms from the group of S, O and N, preferred examples being benzofuranyl, benzothiophenyl, quinolinyl, furyl, imidazolyl, indazolyl, indolyl, isoquinolinyl, oxazolyl, pyridazinyl, pyridyl, pyrimidyl, pyrrolyl, thiazolyl, thienyl, pyrazolyl, isoxazolyl, pyrazinyl, quinolyl or tetrazolyl, which may be monosubstituted by $C_1$-$C_4$-alkyl.

Aralkyl represents aralkyl groups which may contain up to 14 carbon atoms, preferably 6-10 carbon atoms, in the ring and 1-8, preferably 1-4, carbon atoms in the alkyl chain. Useful aralkyl radicals include, for example, benzyl, phenylethyl, naphthylmethyl, naphthylethyl, furylmethyl, thienylethyl, pyridylpropyl. The rings may be mono- or polysubstituted by halogen, OH, O-alkyl, $CO_2H$, $CO_2$-alkyl, $NH_2$, $NH(C_1$-$C_{10}$-alkyl), $N(C_1$-$C_{10}$-alkyl)$_2$, $NO_2$, $N_3$, CN, $C_1$-$C_{20}$-alkyl, $C_1$-$C_{10}$-perfluoroalkyl, $C_1$-$C_{20}$-acyl, $C_1$-$C_{20}$-acyloxy groups.

When radicals in the inventive compounds are substituted, the radicals, unless specified otherwise, may be mono- or polysubstituted. In the context of the present invention, all radicals which occur more than once are each defined independently of one another. Substitution by one, two or three identical or different substituents is preferred. Very particular preference is given to substitution by one substituent.

Preference is given to compounds of the formula (I) in which
the phenyl substituent bearing the $R^1$ and $R^2$ radicals is joined to the phenyl ring in the p position,
n is 0 or 1,
$R^1$ is hydrogen, $C_1$-$C_{10}$-alkyl, $CH_2OR^4$, $CO_2R^5$, CN, aryl or heteroaryl,
$R^2$ is hydrogen or $C_1$-$C_4$-alkyl,
$R^3$ is hydrogen, $C_1$-$C_4$-alkyl, aryl or $C_7$-$C_{12}$-aralkyl,
$R^4$ is hydrogen, —$CH_2$—$CH_2$—OH or $CH_2CO_2R^5$,
$R^5$ is hydrogen or $C_1$-$C_4$-alkyl,
X is oxygen, an $NOR^3$ or =$NNHSO_2R^3$ group,
and the stereoisomers, solvates, salts or solvates of the salts thereof, including all crystal polymorphs, the α-, β- or γ-cyclodextrin clathrates, and the compounds encapsulated with liposomes.

Particular preference is given to compounds of the formula I in which $R^1$ is hydrogen, $C_1$-$C_4$-alkyl, $CH_2OR^4$, $CO_2R^5$, CN, aryl, heteroaryl.

Particular preference is likewise given to compounds of the formula I in which $R^2$ is hydrogen, methyl or ethyl. The preferred $R^2$ radical may be present either in the R or in the S configuration, and in any desired mixing ratio.

Particular preference is further given to compounds of the formula I in which X is oxygen.

Very particular preference is given to compounds of the formula Ia

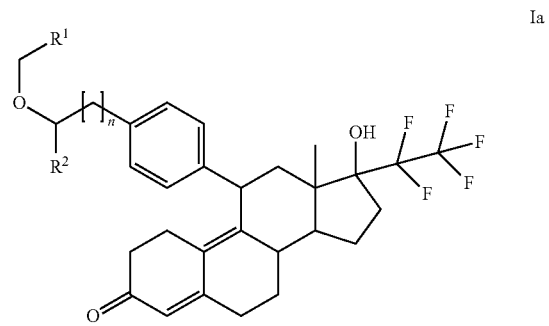

Ia in which
n is 0 or 1
$R^1$ is —H, —$CH_2OH$, —COOH, —COOC($CH_3$)$_3$, —CN or 2-methyl benzothiazol-5-yl
$R^2$ is —H or —$CH_3$
and the stereoisomers, solvates, salts or solvates of the salts thereof, including all crystal polymorphs, the α-, β- or γ-cyclodextrin clathrates, and the compounds encapsulated with liposomes.

The following compounds are especially preferred (additionally incorporated is a reference to the synthesis examples described below):
(8S,11R,13S,14S,17S)-17-hydroxy-11-{4-[(1RS)-1-(2-hydroxyethoxy)ethyl]phenyl}-13-methyl-17-pentafluoroethyl-1,2,6,7,8,11,12,13,14,15,16,17-dodecahydro-cyclopenta[a]phenanthren-3-one (Example 1)

(8S,11R,13S,14S,17S)-17-hydroxy-11-[4-((1RS)-1-methoxyethyl)phenyl]-13-methyl-17-pentafluoroethyl-1,2,6,7,8,11,12,13,14,15,16,17-dodecahydro-cyclopenta[a]phenanthren-3-one (Example 1)

{(1RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)-phenyl]ethoxy}acetic acid tert-butyl ester (Example 2)

{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)-phenyl]prop-2-ynyloxy}acetic acid (Example 3)

{2-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)-phenyl]ethoxy}acetic acid tert-butyl ester (Example 4)

{(RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)-phenyl]ethoxy}acetonitrile (Example 5)

{2-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)-phenyl]ethoxy}acetic acid (Example 6)

(8S,11R,13S,14S,17S)-17-hydroxy-11-{4-[2-(2-hydroxyethoxy)ethyl]phenyl}-13-methyl-17-pentafluoroethyl-1,2,6,7,8,11,12,13,14,15,16,17-dodecahydro-cyclopenta[a]phenanthren-3-one (Example 7)

(8S,11R,13S,14S,17S)-17-hydroxy-13-methyl-11-{4-[(RS)-1-(2-methylbenzothiazol-5-ylmethoxy)ethyl]phenyl}-17-pentafluoroethyl-1,2,6,7,8,11,12,13,14,15,16,17-dodecahydrocyclopenta[a]phenanthren-3-one (Example 8)

The specific radical definitions given in the particular combinations or preferred combinations of radicals are, irrespective of the particular combinations of radicals specified, also replaced as desired by radical definitions of other combinations.

Very particular preference is given to combinations of two or more of the abovementioned preferred ranges.

It has been found that the inventive compounds or derivatives have good progesterone-antagonizing action. In several clinical studies, it has been found that treatment with progesterone antagonists (mifepristone, asoprisnil, Proellex) can lead to significant shrinkage of fibroids of the uterus and to significant reduction of the symptoms associated with these fibroids of the uterus. In addition, it has been found in clinical studies that, during a treatment with the progesterone receptor antagonists mentioned, the symptoms caused by endometriosis (especially pain) can also be distinctly reduced.

The invention further relates to processes for preparing compounds of the formula I, characterized in that compounds of the formula II as described in detail in Examples 1, 2, 4a, 5 and 8 are etherified, any esters present in $R^1$ are hydrolysed as described in detail in Examples 3 and 6, and any protecting groups present in X are detached as described in detail in Examples 4 and 7. The preparation of the inventive compounds can be illustrated by the following synthesis scheme:

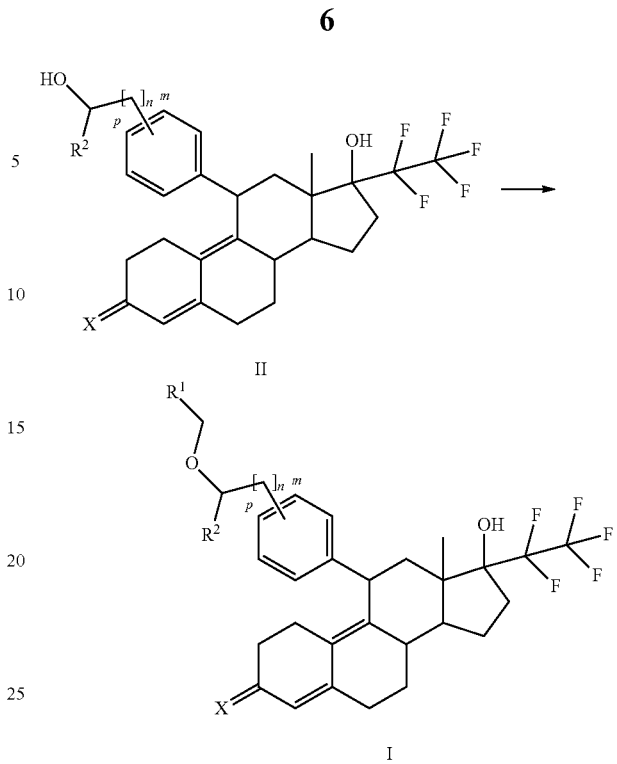

The resulting compounds of the general formula I in which X is an oxygen atom can be converted by reaction with hydroxylamine hydrochloride, alkyloxyamine hydrochlorides or sulphonylhydrazines in the presence of a tertiary amine at temperatures of between −20 and +40° C. to the corresponding E/Z-configured oximes or sulphonylhydrazones thereof (general formula I where X is defined as =NOR$^3$, =NNHSO$_2$R$^3$). Suitable tertiary bases are, for example, trimethylamine, triethylamine, pyridine, N,N-dimethylaminopyridine, 1,5-diazabicyclo[4.3.0]non-5-ene (DBN) and 1,5-diazabicyclo[5.4.0]undec-5-ene (DBU), preference being given to pyridine. An analogous process is described, for example, in WO 98/24801.

The radical definitions given above in general terms or specified within areas of preference apply both to the end products of the formula (I) and correspondingly to the starting materials or intermediates required for the preparation of each.

To the extent that the preparation of the starting compounds is not described here, they are known to the person skilled in the art or are preparable analogously to known compounds or processes described here. The isomer mixtures can be separated into the individual compounds by customary methods, for example crystallization, chromatography or salt formation.

The salts are prepared in a customary manner, by admixing a solution of the compound of the general chemical formula I with the equivalent amount or an excess of a base or acid which may be in solution, optionally removing the precipitate or working up the solution in a customary manner.

The resulting compounds of the formula (I) are optionally reacted with the appropriate solvents and/or bases or acids to give the solvates, salts and/or solvates of the salts thereof.

The inventive compounds exhibit an unforeseeable, valuable pharmacological, pharmacokinetic and pharmacodynamic profile of action.

They are therefore suitable for use as medicaments for treatment and/or prophylaxis of disorders in humans and animals.

The pharmaceutical efficacy of the inventive compounds can be explained by the action thereof as progesterone receptor antagonists, i.e. the antagonizing action thereof on the progesterone receptor.

The present invention further provides for the use of the inventive compounds for treatment and/or prophylaxis of disorders based on hormone-dependent hyper-proliferative processes, preferably of gynaecological disorders, especially of fibroids of the uterus, endometriosis or hormone-dependent breast cancers.

The present invention further provides for the use of the inventive compounds for treatment and/or prophylaxis of disorders, especially of the aforementioned disorders.

The present invention further provides the inventive compounds for use in a process for treatment and/or prophylaxis of fibroids of the uterus, of endometriosis and of hormone-dependent breast cancers.

The present invention further provides for the use of the inventive compounds for production of a medicament for treatment and/or prophylaxis of disorders, especially of the aforementioned disorders.

The present invention further provides a method for treatment and/or prophylaxis of disorders, especially of the aforementioned disorders, using 0.1-100 mg of the inventive compounds per day and patient in the treatment of fibroids of the uterus or of endometriosis, and for the contraceptive use, or of 0.1-500 mg of the inventive compounds per day and patient in the event of tumours (e.g. menginioma or hormone-dependent tumours, for example breast cancer) and in emergency contraception.

The present invention further provides medicaments comprising at least one inventive compound and at least one or more than one further active ingredient, especially for treatment and/or prophylaxis of the aforementioned disorders.

For treatment of tumour disorders, it is possible, for example, to either simultaneously or sequentially administer the following active ingredients/active ingredient classes: SERMs, SERDs, antioestrogens, aromatase inhibitors, kinase inhibitors, angiogenesis inhibitors and/or cytostatics.

For treatment of fibroids of the uterus or of endometriosis, the inventive compounds can be combined simultaneously or sequentially with gestagens or combinations of oestrogens and gestagens.

WO 96/15794 (Spicer et al., Balance Pharm. Inc.), WO 96/03130 (Stöckemann et al., Schering AG) and PCT/EP2009/003249 (Moller et al., Bayer Schering Pharma AG) disclose progesterone receptor antagonist/gestagen regimens. Fibroids of the uterus and endometriosis are very suitably treated by optionally repeating regimens in which the progesterone receptor antagonist is administered over a period of two to four months, followed by the administration of the gestagen over a period of one to four weeks. A particularly suitable administration is the optionally repeating 84-day administration of the progesterone receptor antagonist, followed by the 14-day administration of the gestagen.

For treatment of complaints associated with the menopause, one option is a simultaneous or sequential administration of the inventive compounds, for example, with SERMs, SERDs and oestrogens.

SERMs (Selective Estrogen Receptor Modulators) are medicaments which mediate their action via oestrogen receptors but do not cause antagonistic action in all tissues. These include clomifene, raloxifene, tamoxifene, torimifene, bazedoxifene, lasofoxifene and ormeloxifene.

Selective oestrogen receptor destabilizers (SERDs) are medicaments which antagonise the oestrogen receptor ("pure antioestrogens" without an oestrogenic active component) and lead to partial degradation of the receptor (for example fulvestrant, ZK-703 and ZK-253 (Hoffmann J et al., J Natl Cancer Inst 2004, 96:210-218), and compounds described in WO 98/007740, WO 99/33855 and WO 03/045972.

Antioestrogens are compounds which antagonise the oestrogen receptor, for example fulvestrant.

Aromatase inhibitors inhibit the enzyme aromatase and hence the aromatisation of androgens in oestrogens. These include anastrozole, letrozole, exemestane, vorozole, formestane and fadrozole.

Kinase inhibitors inhibit enzymes which transfer a phosphate residue from ATP to other substrates, and especially to hydroxyl groups therein, for example sorafenib (Nexavar) or imatinib (Gleevec).

Angiogenesis inhibitors, e.g. avastatin, reduce or block new vessel formation and hence the profusion of a tumour.

Cytostatics, e.g. cis-platin, taxol, taxotere, sagopilone, ixabepilone, are natural or synthetic substances which drive tumour cells to apoptosis.

Gestagens in the context of the present invention are understood to mean either natural progesterone itself or synthetic derivatives which, like progesterone itself, bind to the progesterone receptor and inhibit ovulation in doses above the ovulation-inhibiting dose. Examples of synthetic derivatives include drospirenone, gestodene, levonorgestrel, cyproterone acetate, desogestrel and 3-ketodesogestrel, norethisterone, norethisterone acetate and dienogest.

Combinations of gestagens and oestrogens are active ingredient combinations present in the oral contraceptives known per se, for example Yasmin, Femovan, Triquilar, Marvelon, YAZ etc.

The inventive compounds can act systemically and/or locally. For this purpose, they can be administered in a suitable manner, for example by an oral, intrauterine, intravaginal, parenteral, pulmonary, nasal, sublingual, lingual, buccal, rectal, dermal, transdermal, conjunctival or otic route, or as an implant or stent.

"Intrauterine" means especially administration by means of an IUS (intrauterine system) or IUD (intrauterine device). One method of intravaginal administration is by means of an IVR (vaginal ring).

Intrauterine or intravaginal administration forms (cf., for example, WO 01/47490, especially page 1 line 10 to page 5 line 13 and page 7 line 19 to page 58 line 6, or for vaginal rings: WO 06/010097, especially page 10 line 22 to page 14 line 28) may comprise the inventive compounds and nonsilicone and/or silicone polymers, especially also siloxane-based elastomers (cf. WO 01/47490, especially page 7 line 19—page 15 line 15).

For these administration routes, the inventive compounds can be administered in suitable administration forms.

Suitable administration forms for oral administration are those which release the inventive compounds in a rapid and/or modified manner, work according to the prior art and contain the inventive compounds in crystalline and/or amorphous and/or dissolved form, for example tablets (uncoated or coated tablets, for example with enteric or retarded-dissolution or insoluble coatings which control the release of the inventive compound), tablets or films/wafers which disintegrate rapidly in the oral cavity, films/lyophilisates, capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardial, intraspinal or intralumbar route) or with inclusion of an absorption (for example by an intramus- 'cular, subcutaneous, intracutaneous, percutaneous or intraperitoneal route). Suitable administration forms for parenteral administration include injection and infusion formulations in the form of solutions, suspensions, emulsions, lyophilisates or sterile powders.

For the other administration routes, suitable examples are inhalation medicaments (including powder inhalers, nebulizers), nasal drops, solutions or sprays; tablets for lingual, sublingual or buccal administration, films/wafers or capsules, suppositories, ear or eye preparations, vaginal capsules, aqueous suspensions (lotions, shaking mixtures), lipophilic suspensions, ointments, creams, transdermal therapeutic systems (for example patches), milk, pastes, foams, dusting powders, implants or stents.

The inventive compounds can be converted to the administration forms listed. This can be accomplished in a manner known per se by mixing with inert nontoxic pharmaceutically suitable excipients. These excipients include carriers (for example microcrystalline cellulose, lactose, mannitol), solvents (e.g. liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and taste and/or odour correctors.

The present invention further provides medicaments which comprise at least one inventive compound, typically together with one or more inert nontoxic pharmaceutically suitable excipients, and for the use thereof for the aforementioned purposes.

In spite of this, it may be necessary to deviate from the amounts specified, specifically depending on body weight, administration route, individual behaviour towards the active ingredient, type of formulation, and time or interval of administration. For instance, less than the aforementioned minimum amount may be sufficient in some cases, while the upper limit mentioned has to be exceeded in other cases. In the case of administration of greater amounts, it may be advisable to divide them into several individual doses over the day.

The percentages in the tests and examples which follow are percentages by weight unless stated otherwise; parts are parts by weight. Solvent ratios, dilution ratios and concentration figures for liquid/liquid solutions are each based on volume.

The examples which follow serve to illustrate the invention without restricting it in any way.

EXAMPLE 1

(8S,11R,13S,14S,17S)-17-hydroxy-11-{4-[(1RS)-1-(2-hydroxyethoxy)ethyl]phenyl}-13-methyl-17-pentafluoroethyl-1,2,6,7,8,11,12,13,14,15,16,17-dodecahydro-cyclopenta[a]phenanthren-3-one (A) and (8S,11R,13S,14S,17S)-17-hydroxy-11-[4-((1RS)-1-methoxyethyl)phenyl]-13-methyl-17-pentafluoroethyl-1,2,6,7,8,11,12,13,14,15,16,17-dodecahydrocyclopenta[a]phenanthren-3-one (B)

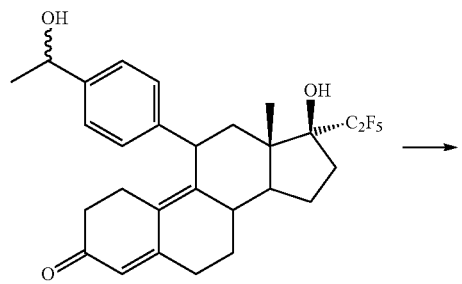

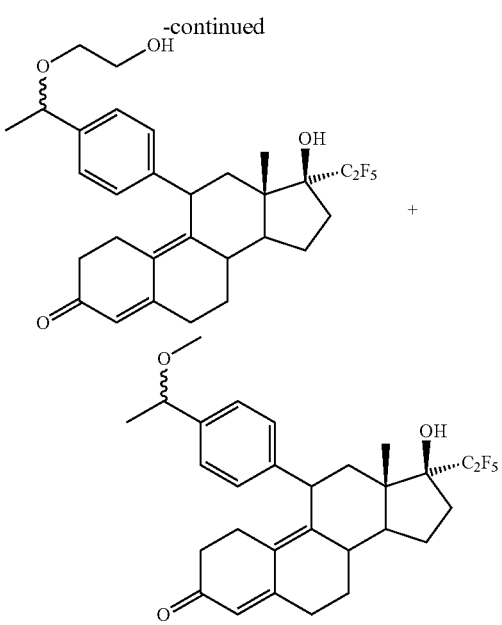

The solution of 1.0 g (1.96 mmol) of (8S,11R,13S,14S,17S)-17-hydroxy-11-[4-((RS)-1-hydroxyethyl)phenyl]-13-methyl-17-pentafluoroethyl-1,2,6,7,8,11,12,13,14,15,16,17-dodecahydrocyclopenta[a]phenanthren-3-one (cf. WO 98/34947, Ex. 13, page 22) in 10 ml of dichloromethane was admixed with 0.55 ml of ethylene glycol, 0.43 ml of trimethyl orthoformate and 20 mg of p-toluenesulphonic acid monohydrate, and the mixture was stirred at 23° C. for 48 hours. The mixture was admixed with saturated sodium hydrogencarbonate solution and extracted repeatedly with dichloromethane, and the combined organic extracts were dried over sodium sulphate. The residue obtained after filtration and removal of the solvent was purified by chromatography. 277 mg (26%) of title compound A and 192 mg (19%) of title compound B were isolated, each as a colourless foam.

$^1$H NMR (CDCl$_3$) of A: δ=0.59 (3H), 1.44 (3H), 1.41-1.54 (2H), 1.74-1.85 (3H), 1.97-2.10 (2H), 2.13 (1H), 2.25-2.64 (9H), 2.75 (1H), 3.40 (2H), 3.68 (2H), 4.43 (2H), 5.78 (1H), 7.14 (2H), 7.22 (2H) ppm.

$^1$H NMR (CDCl$_3$) of B: δ=0.60 (3H), 1.42 (3H), 1.38-1.54 (2H), 1.73-1.87 (3H), 2.01-2.14 (2H), 2.24-2.65 (9H), 2.75 (1H), 3.21 (3H), 4.27 (1H), 4.46 (1H), 5.79 (1H), 7.17 (2H), 7.22 (2H) ppm.

EXAMPLE 2

{(1RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethoxy}acetic acid tert-butyl ester (A) and {(8S,11R,13S,14S,17S)-11-[4-((RS)-1-tert-butoxycarbonylmethoxyethyl)phenyl]-13-methyl-3-oxo-17-pentafluoroethyl-2,3,6,7,8,11,12,13,14,15,16,17-dodecahydro-1H-cyclopenta[a]phenanthren-17-yloxy}acetic acid tert-butyl ester (B)

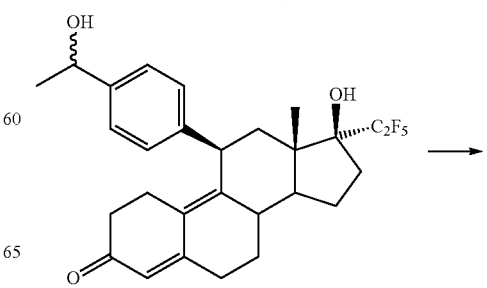

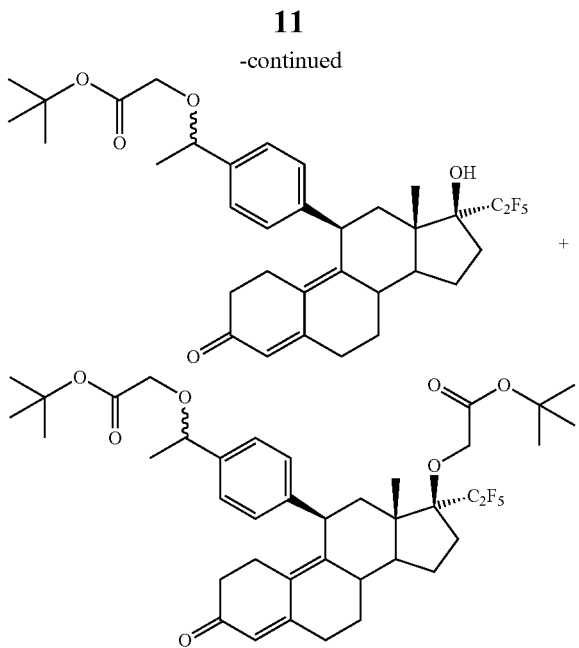

The solution of 500 mg (0.98 mmol) of (8S,11R,13S,14S, 17S)-17-hydroxy-11-[4-((RS)-1-hydroxyethyl)phenyl]-13-methyl-17-pentafluoroethyl-1,2,6,7,8,11,12,13,14,15,16,17-dodecahydrocyclopenta[a]phenanthren-3-one in 1.5 ml of dichloromethane was admixed with 0.81 ml of tert-butyl bromoacetate, 2.3 ml of a 50% potassium hydroxide solution and 13 mg of tetrabutylammonium hydrogensulphate, and the mixture was stirred at 23° C. for 2 hours. The mixture was diluted with water and dichloromethane, acidified by adding 4 molar hydrochloric acid and extracted with dichloromethane. The combined organic extracts were dried over sodium sulphate. The residue obtained after filtration and removal of the solvent was purified by chromatography. 155 mg (21%) of title compound A and 84 mg (14%) of title compound B were isolated, each as a colourless foam.

$^{1}$H NMR (CDCl$_{3}$) of A: δ=0.64 (3H), 1.50 (9H), 1.53 (3H), 1.43-1.57 (2H), 1.78-1.91 (3H), 2.06-2.16 (2H), 2.28-2.69 (9H), 2.79 (1H), 3.78 (1H), 3.92 (1H), 4.49 (1H), 4.56 (1H), 5.83 (1H), 7.19 (2H), 7.29 (2H) ppm.

$^{1}$H NMR (CDCl$_{3}$) of B: δ=0.69 (3H), 1.44 (9H), 1.50 (9H), 1.52 (3H), 1.39-1.59 (2H), 1.77-1.96 (2H), 2.03-2.15 (2H), 2.28-2.85 (10H), 3.76 (1H), 3.91 (1H), 4.11 (2H), 4.47 (1H), 4.55 (1H), 5.82 (1H), 7.20 (2H), 7.28 (2H) ppm.

EXAMPLE 3

{(RS)-1-[4-((8S,11R,13S,14S,17S)-17-hydroxy-13-methyl-3-oxo-17-pentafluoroethyl-2,3,6,7,8,11,12, 13,14,15,16,17-dodecahydro-1H-cyclopenta[a] phenanthren-11-yl)phenyl]ethoxy}acetic acid

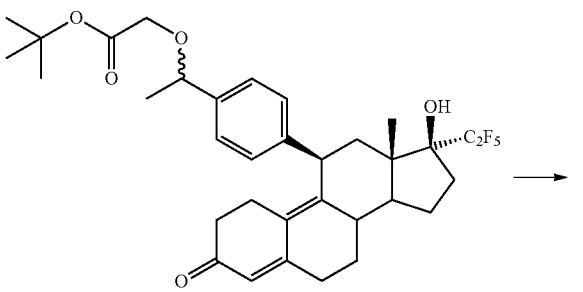

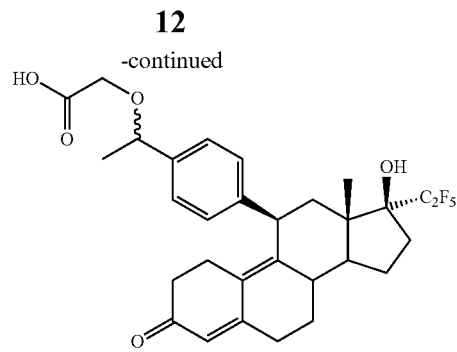

The solution of 57 mg (91 pmol) of compound A prepared according to Example 2 in 1 ml of tetrahydrofuran was admixed with 0.4 ml of a 5% aqueous lithium hydroxide solution and the mixture was stirred at 23° C. for 1 hour. The mixture was admixed with 250 pl of a 1 molar sodium hydroxide solution and 0.5 ml of methanol, and the mixture was stirred for a further 2 hours. It was acidified by adding 1 molar hydrochloric acid, saturated with sodium chloride and extracted repeatedly with ethyl acetate, and the combined organic extracts were dried over sodium sulphate. The residue obtained after filtration and removal of the solvent was purified by chromatography. 37 mg (71%) of the title compound were isolated.

$^{1}$H NMR (CD$_{3}$OD): δ=0.58 (3H), 1.42 (3H), 1.37-1.54 (2H), 1.70-1.82 (3H), 2.09 (1H), 2.18-2.47 (5H), 2.55-2.72 (4H), 2.81 (1H), 3.29 (2H), 3.54-3.74 (2H), 4.45-4.55 (2H), 5.73 (1H), 7.21 (2H), 7.26 (2H) ppm.

EXAMPLE 4

{2-[4-((8S,11R,13S,14S,17S)-17-hydroxy-13-methyl-3-oxo-17-pentafluoroethyl-2,3,6,7,8,11,12,13, 14,15,16,17-dodecahydro-1H-cyclopenta[a]phenanthren-11-yl)-phenyl]ethoxy}acetic acid tert-butyl ester

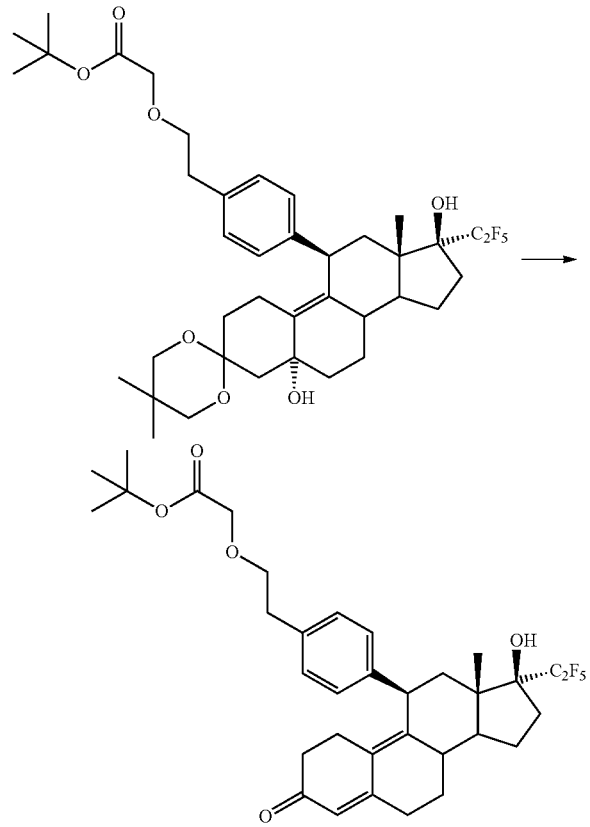

The solution of 90 mg (0.1 mmol) of the compound prepared according to Example 4a in 2.4 ml of acetone was admixed with 160 pl of 4N hydrochloric acid and the mixture was stirred at 23° C. for 2 hours. It was poured into a saturated sodium hydrogencarbonate solution and extracted repeatedly with dichloromethane, the combined organic extracts were dried over sodium sulphate and the residue obtained after filtration and removal of the solvent was purified by chromatography. 37 mg (60%) of the title compound were isolated as a colourless foam.

$^1$H NMR (CDCl$_3$): δ=0.59 (3H), 1.47 (9H), 1.40-1.53 (2H), 1.74-1.86 (3H), 2.05 (2H), 2.23-2.63 (9H), 2.72 (1H), 2.91 (2H), 3.72 (2H), 3.96 (2H), 4.42 (1H), 5.77 (1H), 7.09 (2H), 7.15 (2H) ppm.

EXAMPLE 4a

{2-[4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]-phenanthrene-3,2'-[1,3]dioxane]-11-yl)phenyl]ethoxy}acetic acid tert-butyl ester

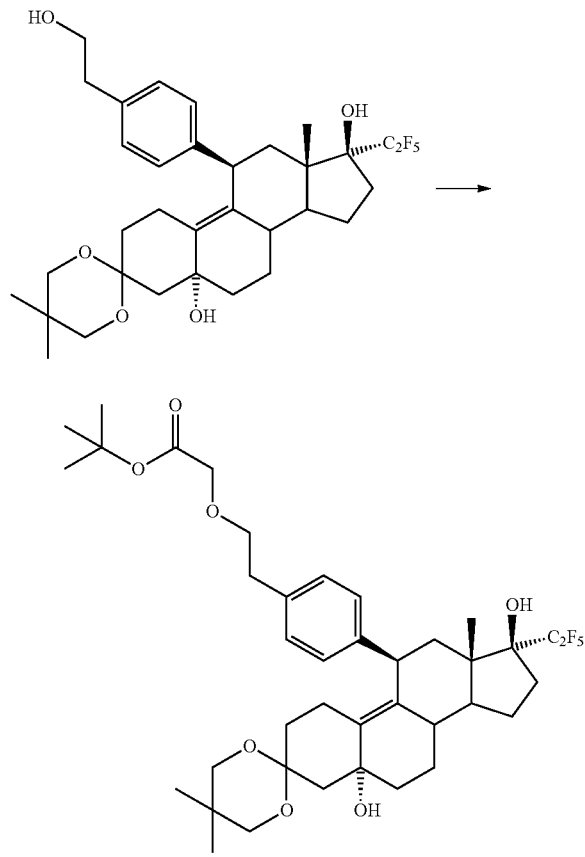

In analogy to Example 2, 250 mg (0.41 mmol) of the compound prepared according to Example 4b were converted and, after workup and purification, 181 mg (61%) of the title compound were isolated as a colourless foam.

EXAMPLE 4b (5R,8S,11R,13S,14S,17S)-11-[4-(2-hydroxyethyl)phenyl]-5',5',13-trimethyl-17-pentafluoroethyl-1,2,3,4,6,7,8,11,12,13,14,15,16,17-tetradecahydro-1H-spiro[cyclopenta[a]phenanthrene-3,2'-[1,3]dioxane]-5,17-diol

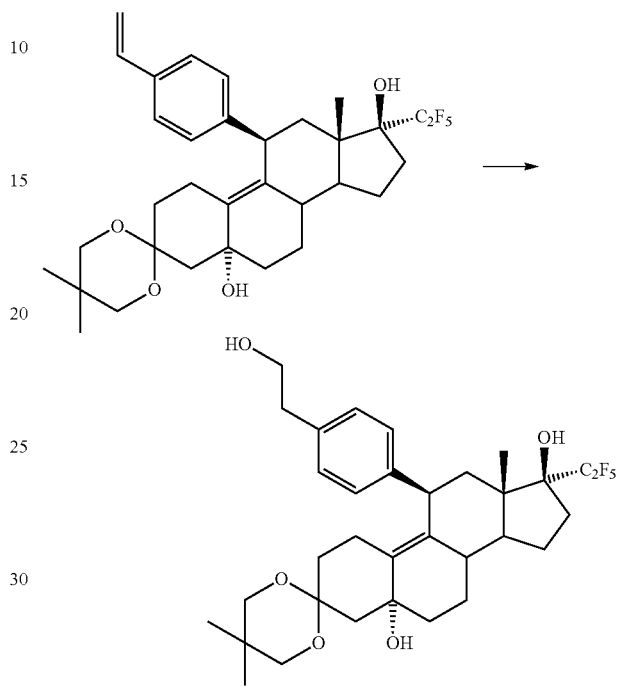

To the solution of 2.0 g (3.35 mmol) of the compound prepared according to Example 4c in 20 ml of tetrahydrofuran were added dropwise 25 ml of a 0.5 molar solution of 9-borabicyclo[3.3.1]nonane in tetrahydrofuran and the mixture was stirred at 23° C. for 4 hours. The mixture was cooled to 3° C., 11 ml of a 5% sodium hydroxide solution and 2.9 ml of a 30% hydrogen peroxide solution were added, and the mixture was stirred overnight. The mixture was extracted repeatedly with ethyl acetate, washed with water and a saturated sodium thiosulphate solution and dried over sodium sulphate. The residue obtained after filtration and removal of the solvent was purified by chromatography. 1.5 g (73%) of the title compound were isolated as a colourless foam.

EXAMPLE 4c (5R,8S,11R,13S,14S,17S)-11-(4-ethenylphenyl)-5',5',13-trimethyl-17-(pentafluoroethyl)-1,2,3,4,6,7,8,11,12,13,14,15,16,17-tetradecahydrospiro[cyclopenta[a]phenanthrene-3,2'-[1,3]dioxane]-5,17-diol

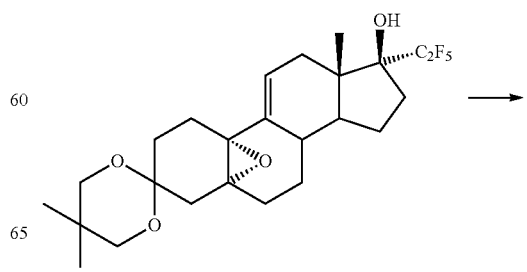

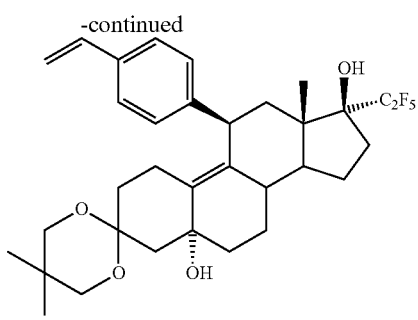

2.22 g of magnesium turnings and a solution of 11.95 ml of 4-bromostyrene in 75 ml of tetrahydrofuran were used to prepare the Grignard reagent, with gentle heating to 30-50° C. and optionally with addition of an iodine crystal. The mixture was cooled to 5° C., 117 mg of copper(I) chloride were added, and the solution of 15 g (30.5 mmol) of (5R,8S,10R,13S,14S,17S)-17-(pentafluoroethyl)-5,10-epoxy-5',5',13-trimethyl-1,2,3,4,6,7,8,12,13,14,15,16,17-tridecahydrospiro[cyclopenta[a]phenanthren-3,2'-[1,3]dioxane]-17-ol, which was prepared by the process described in DE 102006054535, in 150 ml was added dropwise. The mixture was stirred at 23° C. for 1 hour, diluted with ethyl acetate and poured into a saturated ammonium chloride solution. The aqueous phase was extracted repeatedly with ethyl acetate, and the combined organic extracts were washed with saturated sodium chloride solution and dried over sodium sulphate. The solid obtained after filtration and removal of solvent was recrystallized from hexane, and 16.6 g (91%) of the title compound were isolated as a colourless solid.

EXAMPLE 5

{(RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethoxy}acetonitrile

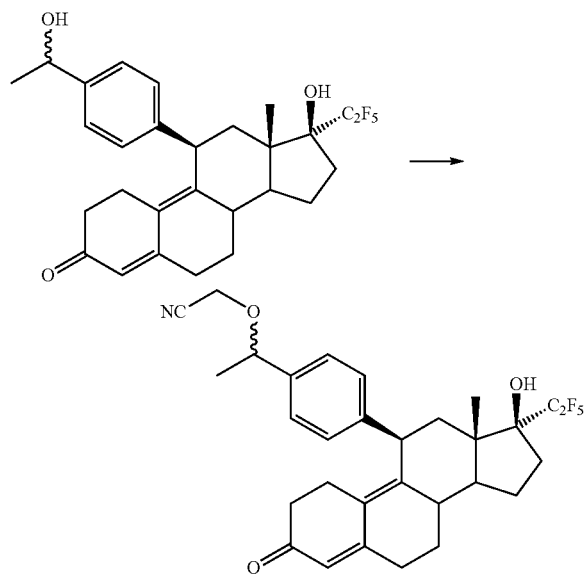

In analogy to Example 2, 250 mg (0.39 mmol) of (8S,11R,13S,14S,17S)-17-hydroxy-11-[4-((RS)-1-hydroxyethyl)phenyl]-13-methyl-17-pentafluoroethyl-1,2,6,7,8,11,12,13,14,15,16,17-dodecahydrocyclopenta[a]phenanthren-3-one were converted using bromoacetonitrile and, after workup and purification, 16 mg (8%) of the title compound were isolated as a colourless foam.

$^1$H NMR (CDCl$_3$): δ=0.59 (3H), 1.38-1.57 (2H), 1.50 (3H), 1.73-1.87 (3H), 2.02-2.12 (2H), 2.22-2.64 (9H), 2.75 (1H), 3.89+3.94 (1H), 4.14+4.19 (1H), 4.46 (1H), 4.61 (1H), 5.79 (1H), 7.19 (2H), 7.25 (2H) ppm.

EXAMPLE 6

{2-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)-phenyl]ethoxy}acetic acid

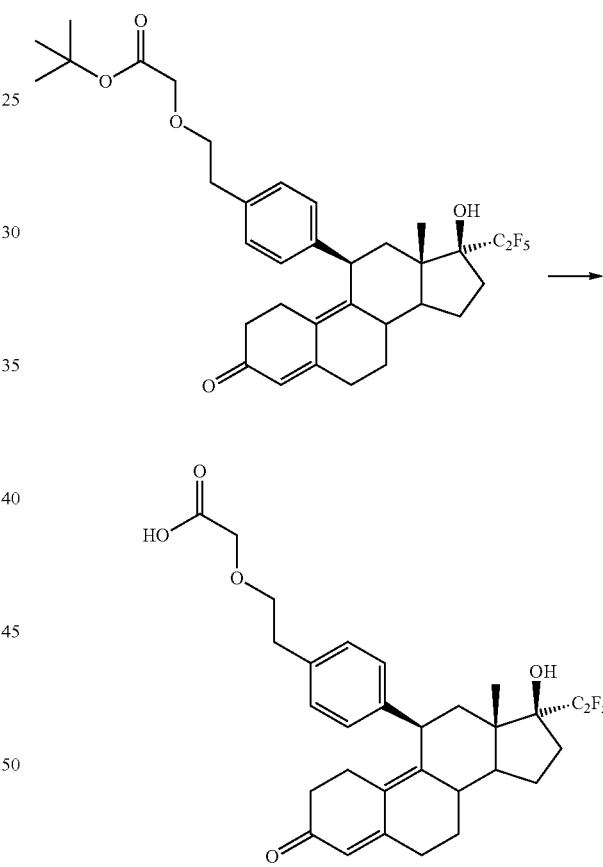

The solution of 32 mg (51 pmol) of the compound prepared according to Example 4 in 1.4 ml of dichloromethane was admixed with 140 μl of trifluoroacetic acid and the mixture was stirred at 23° C. for 2.5 hours. Toluene was added, the mixture was concentrated and the residue was purified by chromatography. 25.8 mg (89%) of the title compound were isolated as a colourless foam.

$^1$H NMR (CD$_3$OD): δ=0.58 (3H), 1.36-1.54 (2H), 1.70-1.82 (3H), 2.08 (1H), 2.18-2.46 (5H), 2.54-2.90 (7H), 3.64 (2H), 3.84 (2H), 4.48 (1H), 5.73 (1H), 7.13 (2H), 7.17 (2H) ppm.

EXAMPLE 7

(8S,11R,13S,14S,17S)-17-hydroxy-11-{4-[2-(2-hydroxyethoxy)ethyl]phenyl}-13-methyl-17-pentafluoroethyl-1,2,6,7,8,11,12,13,14,15,16,17-dodecahydro-cyclopenta[a]phenanthren-3-one

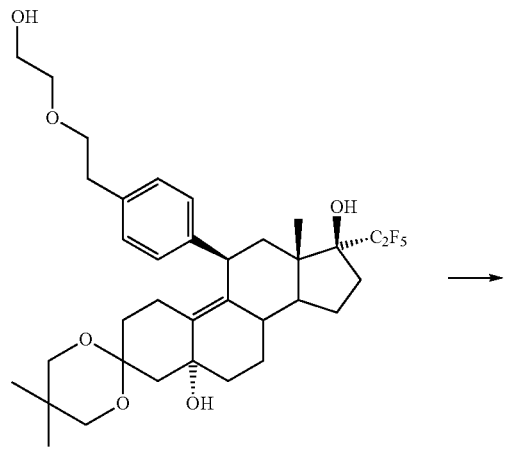

In analogy to Example 4, 64 mg (58 µmol) of the compound prepared according to Example 7a were converted and, after workup and purification, 12 mg (38%) of the title compound were isolated as a colourless foam.

$^1$H NMR (CDCl$_3$): δ=0.59 (3H), 1.40-1.55 (2H), 1.73-1.92 (4H), 2.05 (1H), 2.22 (1H), 2.24-2.63 (9H), 2.73 (1H), 2.86 (2H), 3.53 (2H), 3.63-3.74 (4H), 4.43 (1H), 5.78 (1H), 7.09 (2H), 7.13 (2H) ppm.

EXAMPLE 7a (5R,8S,11R,13S,14S,17S)-11-{4-[2-(2-hydroxyethoxy)ethyl]phenyl}-5',5',13-trimethyl-17-pentafluoroethyl-1,2,3,4,6,7,8,11,12,13,14,15,16,17-tetradecahydro-1H-spiro[cyclopenta[a]phenanthrene-3,2'-[1,3]dioxane]-5,17-diol

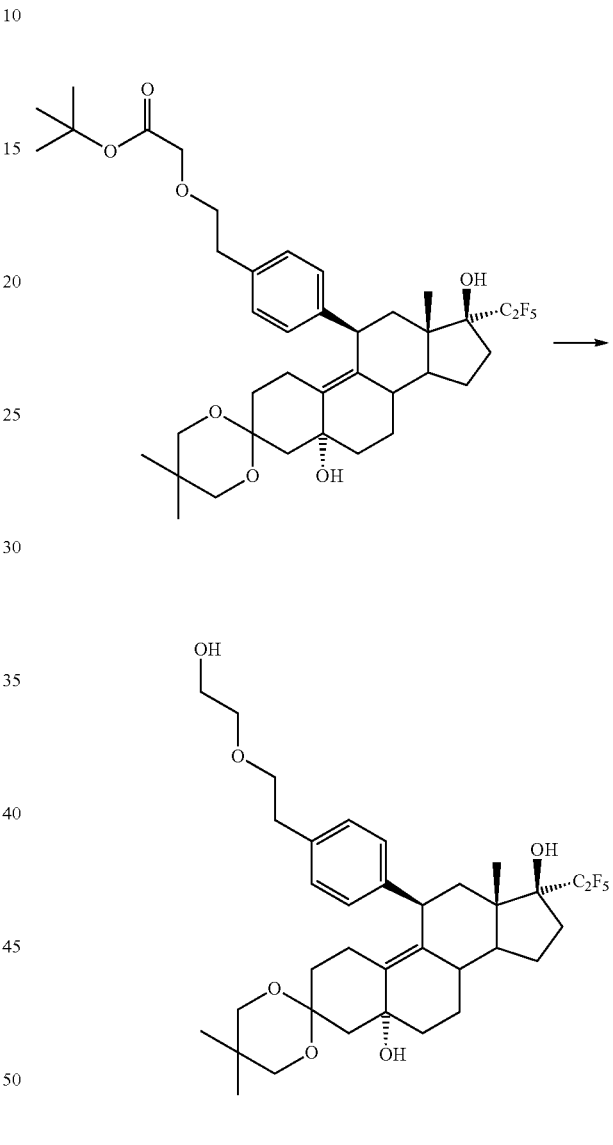

The solution of 83 mg (91 mmol) of the compound prepared according to Example 4a in 2 ml of toluene was admixed at 0° C. with 310 µl of a 1 molar solution of diisobutylaluminium hydride in toluene. After 1 hour, the mixture was poured into saturated ammonium chloride solution and extracted repeatedly with ethyl acetate, and the combined organic extracts were washed with saturated sodium chloride solution and dried over sodium sulphate. The residue obtained after filtration and removal of the solvent was purified by chromatography. 58 mg (97%) of the title compound were isolated as a colourless foam.

EXAMPLE 8

(8S,11R,13S,14S,17S)-17-hydroxy-13-methyl-11-{4-[(RS)-1-(2-methylbenzothiazol-5-ylmethoxy)ethyl]phenyl}-17-pentafluoroethyl-1,2,6,7,8,11,12,13,14,15,16,17-dodecahydro-cyclopenta[a]phenanthren-3-one

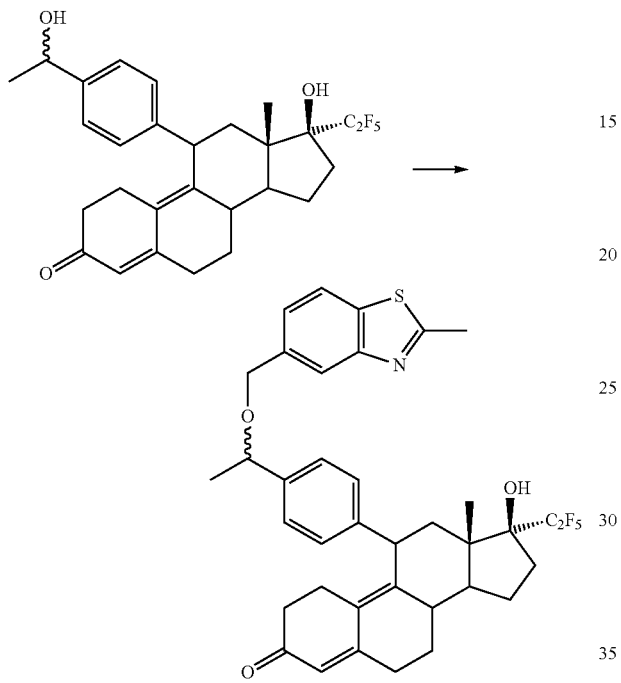

In analogy to Example 2, 500 mg (0.98 mmol) of (8S,11R,13S,14S,17S)-17-hydroxy-11-[4-((RS)-1-hydroxyethyl)phenyl]-13-methyl-17-pentafluoroethyl-1,2,6,7,8,11,12,13,14,15,16,17-dodecahydrocyclopenta[a]phenanthren-3-one were converted using 5-bromomethyl-2-methylbenzothiazole and, after workup and purification, 157 mg (24%) of the title compound were isolated as a colourless foam.

$^1$H NMR (CDCl$_3$): δ=0.61+0.63 (3H), 1.47 (3H), 1.39-1.57 (2H), 1.73-1.88 (3H), 2.01-2.14 (2H), 2.26-2.66 (9H), 2.77 (1H), 2.92+2.93 (3H), 4.38-4.55 (4H), 5.79 (1H), 7.17 (2H), 7.25-7.33 (3H), 7.74-7.85 (2H) ppm.

EXAMPLE 9

Progesterone Receptor-Antagonistic Action in Stable Transfectants of Human Neuroblastoma Cells (SK-N-MC Cells) with the Human Progesterone A or Progesterone B Receptor and an MN-LUC Reporter Construct SK-N-MC cells (human neuroblastoma cells) which have been stably transfected with plasmids expressing the human progesterone receptor B (pRChPR-B-neo) or the human progesterone receptor A (pRChPR-A-neo) and a reporter construct (pMMTV-LUC) were incubated for 24 hours either in the absence (negative control) or in the presence of ascending amounts of the particular test compound (0.01 nmol/l, 0.1 nmol/l, 1 nmol/l, 10 nmol/l, 100 nmol/l and 1 pmol/l), in order to determine the agonistic efficacy. As a positive control of the reporter gene induction, the cells were treated with the synthetic gestagen promegestone (0.01 nmol/l, 0.1 nmol/l, 1 nmol/l, 10 nmol/l, 100 nmol/l and 1 pmol/l). To determine the antagonistic activity, the cells were treated with 0.1 nmol/l promegestone and additionally with ascending amounts of the particular test compound (0.01 nmol/l, 0.1 nmol/l, 1 nmol/l, 10 nmol/l, 100 nmol/l and 1 pmol/l). The activity of the reporter gene LUC (LUC=luciferase) was determined in the cell lysates and measured as RLU (relative light units). All measurements are reported as % efficacy and as EC$_{50}$ and EC$_{50}$ concentrations.

a) Agonistic activity: none of the compounds mentioned exhibits agonistic activity.

b) Antagonistic activity: all compounds mentioned exhibit 100% antagonistic efficacy.

The antagonistic potency of the compounds is summarized in Table 1.

TABLE 1

| | Antagonistic potency of the compounds | |
|---|---|---|
| Ex. | PR-A IC$_{50}$ [nM] | PR-B IC$_{50}$ [nM] |
| 1A | 0.12 | 0.36 |
| 1B | 0.1 | 0.1 |
| 2 | 0.1 | 0.12 |
| 3 | 13 | 9.8 |
| 4 | 0.1 | 0.1 |
| 5 | 0.1 | 0.1 |
| 6 | 3 | 12 |
| 7 | 0.1 | 0.1 |
| 8 | 0.06 | 0.1 |

The invention claimed is:

1. Compound of the formula I

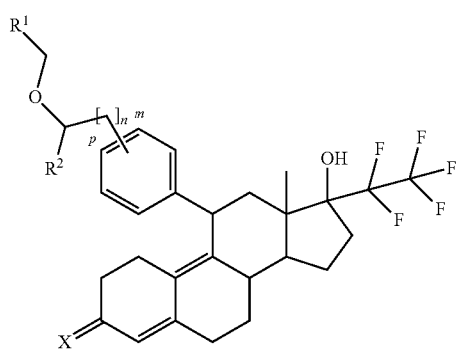

in which
the phenyl substituent bearing the R$^1$ and R$^2$ radicals is joined to the phenyl ring in the
m or p position,
n is 0 or 1,
R$^1$ is hydrogen, C$_1$-C$_{10}$-alkyl, CH$_2$OR$^4$, CO$_2$R$^5$, CN, aryl or heteroaryl,
R$^2$ is hydrogen or C$_1$-C$_{10}$-alkyl,
R$^3$ is hydrogen, C$_1$-C$_{10}$-alkyl, aryl or C$_7$-C$_{20}$-aralkyl,
R$^4$ is hydrogen, —CH$_2$-CH$_2$—OH or CH$_2$CO$_2$R$^5$,
R$^5$ is hydrogen or C$_1$-C$_{10}$-alkyl,
X is oxygen, an NOR$^3$ or =NNHSO$_2$R$^3$ group, and the stereoisomers, or the salts thereof, and the α-, (β- or γ-cyclodextrin clathrates thereof.

2. Compound according to claim 1 in which R$^1$ is hydrogen, C$_1$-C$_4$-alkyl, CH$_2$OR$^4$, CO$_2$R$^5$, CN, aryl or heteroaryl.

3. Compound according to claim 1 in which R$^2$ is hydrogen, methyl or ethyl.

4. Compound according to claim 1 in which X is oxygen.

5. Compound according to claim 1 in which the phenyl substituent bearing the $R^1$ and $R^2$ radicals is joined to the phenyl ring in the
p position,
n is 0 or 1,
$R^1$ is hydrogen, $C_1$-$C_{10}$-alkyl, $CH_2OR^4$, $CO_2R^5$, CN, aryl or heteroaryl,
$R^2$ is hydrogen or $C_1$-$C_4$-alkyl,
$R^3$ is hydrogen, $C_1$-$C_4$-alkyl, aryl or $C_7$-$C_{12}$-aralkyl,
$R^4$ is hydrogen, —$CH_2$—$CH_2$—OH or $CH_2CO_2R^5$,
$R^5$ is hydrogen or $C_1$-$C_4$-alkyl, and
X is oxygen, an $NOR^3$ or $=NNHSO_2R^3$ group.

6. Compound according to claim 1 of the formula Ia:

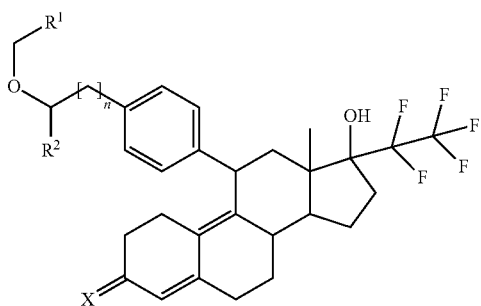

in which
n is 0 or 1,
$R^1$ is —H, —$CH_2OH$, —COOH, —COOC($CH_3$)$_3$, —CN or 2-methylbenzothiazol-5-yl, and
$R^2$ is —H or —$CH_3$.

7. A compound that is (8S, 11R, 13S,14S, 17S)-17-hydroxy-11-{4-[(1RS)-1-(2-hydroxyethoxy)ethyl]-phenyl}-13-methyl-17-pentafluoroethyl-1,2,6,7,8,11,12,13,14,15,16,17-dodecahydrocyclopenta[a]phenanthren-3-one,
(8S,11R,13S,14S,17S)-17-hydroxy-11-[4-((1RS)-1-methoxyethyl)phenyl]-13-methyl-17-pentafluoroethyl-1,2,6,7,8,11,12,13,14,15,16,17-dodecahydro-cyclopenta[a]phenanthren-3-one,
{(1RS)-1-[4(8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethoxy}acetic acid tert-butyl ester,
{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyloxy}acetic acid,
{2-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethoxy}acetic acid tert-butyl ester,
{(RS)-1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethoxy}acetonitrile,
{2-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]ethoxy}acetic acid,
(8S,11R,13S,14S,17S)-17-hydroxy-11-{4-[2-(2-hydroxyethoxy)ethyl]phenyl}-13-methyl-17-pentafluoroethyl-1,2,6,7,8,11,12,13,14,15,16,17-dodecahydro-cyclopenta[a]phenanthren-3-one or
(8S,11R,13S,14S,17S)-17-hydroxy-13-methyl-11-{4-[(RS)-1-(2-methyl-benzothiazol-5-ylmethoxy)ethyl]phenyl}-17-pentafluoroethyl-1,2,6,7,8,11,12,13,14,15,16,17-dodecahydrocyclopenta[a]phenanthren-3-one.

8. Medicament comprising a compound as defined in claim 1 in combination with one or more inert nontoxic pharmaceutically suitable excipients.

9. Medicament according to claim 8 comprising a further active ingredient selected from SERMs, SERDs, antioestrogens, aromatase inhibitors, kinase inhibitors, angiogenesis inhibitors or cytostatics.

10. Medicament according to claim 8 comprising a further active ingredient selected from gestagens or gestagen/oestrogen combinations.

11. Method for controlling fibroids of the uterus, myomas, uterine leiomyomas, endometriosis, heavy menstrual bleeds, meningiomas, or breast cancer by administering an effective amount of at least one compound as defined in claim 1 to a patient in need thereof.

12. Method for fertility control or emergency contraception by administering an effective amount of at least one compound as defined in claim 1 to a patient in need thereof.

* * * * *